(12) United States Patent
Baldridge et al.

(10) Patent No.: US 7,829,542 B2
(45) Date of Patent: *Nov. 9, 2010

(54) PROPHYLACTIC AND THERAPEUTIC TREATMENT OF INFECTIOUS AND OTHER DISEASES WITH IMMUNOEFFECTOR COMPOUNDS

(75) Inventors: Jory R. Baldridge, Victor, MT (US); David A. Johnson, Hamilton, MT (US); Christopher W. Cluff, Hamilton, MT (US)

(73) Assignee: Corixa Corporation, Seattle, WA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/130,907

(22) Filed: May 30, 2008

(65) Prior Publication Data

US 2008/0227729 A1  Sep. 18, 2008

Related U.S. Application Data

(63) Continuation of application No. 11/107,662, filed on Apr. 14, 2005, now abandoned, which is a continuation of application No. 10/068,398, filed on Feb. 4, 2002, now Pat. No. 6,911,434.

(51) Int. Cl.
*A61K 31/7008* (2006.01)
*A61K 31/7024* (2006.01)
*A61K 31/7056* (2006.01)
*C07H 17/02* (2006.01)

(52) U.S. Cl. .......................... 514/24; 514/27; 514/32; 536/17.4

(58) Field of Classification Search ................... None
See application file for complete search history.

(56) References Cited

U.S. PATENT DOCUMENTS

| | | | |
|---|---|---|---|
| 4,987,237 A | 1/1991 | Myers et al. | |
| 5,508,310 A * | 4/1996 | Rhodes | 514/576 |
| 6,113,918 A | 9/2000 | Johnson et al. | |
| 6,221,388 B1 | 4/2001 | Hersch et al. | |
| 6,303,347 B1 | 10/2001 | Johnson et al. | |
| 6,355,257 B1 | 3/2002 | Johnson et al. | |
| 6,525,028 B1 | 2/2003 | Johnson et al. | |
| 6,531,453 B1 | 3/2003 | Taniguchi et al. | |
| 6,911,434 B2 | 6/2005 | Baldridge et al. | |
| 7,129,219 B2 | 10/2006 | Johnson et al. | |
| 7,501,399 B2 * | 3/2009 | Johnson et al. | 514/27 |
| 2002/0115624 A1 | 8/2002 | Behar et al. | |

FOREIGN PATENT DOCUMENTS

| | | |
|---|---|---|
| HU | 0004147 A2 | 4/2001 |
| WO | WO 98/50399 A1 | 11/1998 |
| WO | WO 00/11010 A1 | 3/2000 |
| WO | WO 01/70209 A1 | 9/2001 |
| WO | WO 01/90129 A2 | 11/2001 |
| WO | WO 01/90129 A3 | 11/2001 |
| WO | WO 02/12258 A1 | 2/2002 |
| WO | WO 03/065806 A | 8/2003 |
| WO | WO 03/066065 A1 | 8/2003 |

OTHER PUBLICATIONS

Merriam-Webster's Collegiate Dictionary, published 1998 by Merriam-Webster, Incorporated, pp. 924 and 935.*
Dorland, I., *Dorland's Illustrated Medical Dictionary*, 30th Edition, Philadelphia, Elsevier, 2003.
Johnson, David A. et al.; "Synthesis and Biological Evaluation of a New Class of Vaccine Adjuvants: Aminoalkyl Glucosaminide 4-Phosphates (AGPs)"; 1999, *Bioorganic & Medicinal Chemistry Letters*, vol. 9, pp. 2273-2278.
Paradisi et al., "Streptococcus pneumoniae as an agent of nosocomal infection: treatment in the era of penicillin-resistant strains," 2001, Clinical Microbiology and Infection, vol. 7, Suppl. 4, pp. 34-42.
Passalacqua et al., "Allergen-Specific Sublingual Immunotherapy for Respiratory Allergy," 2001, BioDrugs, vol. 15, No. 8, pp. 509-519.
Quesniaux, Valerie FJ et al.; "Toll-like receptors: emerging targets of immunomodulation"; 2004, *Expert Opinion* vol. 14, No. 1, pp. 85-100.

* cited by examiner

*Primary Examiner*—Eric S Olson
(74) *Attorney, Agent, or Firm*—Townsend and Townsend and Crew LLP

(57) ABSTRACT

Methods and compositions for treating or ameliorating diseases and other conditions, such as infectious diseases, autoimmune diseases and allergies are provided. The methods employ cyclic AGPs for selectively stimulating immune responses in animals and plants.

17 Claims, No Drawings

US 7,829,542 B2

PROPHYLACTIC AND THERAPEUTIC TREATMENT OF INFECTIOUS AND OTHER DISEASES WITH IMMUNOEFFECTOR COMPOUNDS

This is a continuation of application Ser. No. 11/107,662 filed Apr. 14, 2005, which is a continuation of application Ser. No. 10/068,398 filed Feb. 4, 2002, the entire contents of which are hereby incorporated herein.

BACKGROUND OF THE INVENTION

The innate immune system coordinates the inflammatory response to pathogens by a system that discriminates between self and non-self via receptors that identify classes of molecules synthesized exclusively by microbes. These classes are sometimes referred to as pathogen associated molecular patterns (PAMPs) and include, for example, lipopolysaccharide (LPS), peptidoglycans, lipotechoic acids, and bacterial lipoproteins (BLPs).

LPS, an abundant outer cell-wall constituent from gram-negative bacteria, is recognized by the innate immune system. Although the chemical structure of LPS has been known for some time, the molecular basis of recognition of LPS by serum proteins and/or cells is only now being elucidated. In a series of recent reports, a family of receptors, referred to as Toll-like receptors (TLRs), have been linked to the potent innate immune response to LPS and other microbial components. TLR are membrane proteins having a single transmembrane domain. The cytoplasmic domains are approximately 200 amino acids and share similarity with the cytoplasmic domain of the IL-1 receptor. The extracellular domains are relatively large (about 550-980 amino acids) and may contain multiple ligand-binding sites.

The importance of TLRs in the immune response to LPS has been specifically demonstrated for at least two Toll-like receptors, Tlr2 and Tlr4. For example, transfection studies with embryonic kidney cells revealed that human Tlr2 was sufficient to confer responsiveness to LPS (Yang et al., *Nature* 395:284-288 (1998); Kirschning et al. *J Exp Med.* 11:2091-97 (1998)). A strong response by LPS appeared to require both the LPS-binding protein (LBP) and CD14, which binds LPS with high affinity. Direct binding of LPS to Tlr2 was observed at a relatively low affinity, suggesting that accessory proteins may facilitate binding and/or activation of Tlr2 by LPS in vivo.

The importance of Tlr4 in the immune response to LPS was demonstrated in conjunction with positional cloning in lps mutant mouse strains. Two mutant alleles of the mouse lps gene have been identified, a semidominant allele that arose in the C3H/HeJ strain and a second, recessive allele that is present in the C57BL/10ScN and C57BL/10ScCr strains. Mice that are homozygous for mutant alleles of lps are sensitive to infection by Gram-negative bacteria and are resistant to LPS-induced septic shock. The lps locus from these strains was cloned and it was demonstrated that the mutations altered the mouse Tlr4 gene in both instances (Portorak et al., *Science* 282:2085-2088 (1998); Qureshi et al., *J Exp Med* 4:615-625 (1999)). It was concluded from these reports that Tlr4 was required for a response to LPS.

The biologically active endotoxic sub-structural moiety of LPS is lipid-A, a phosphorylated, multiply fatty-acid-acylated glucosamine disaccharide that serves to anchor the entire structure in the outer membrane of Gram-negative bacteria. We previously reported that the toxic effects of lipid A could be ameliorated by selective chemical modification of lipid A to produce monophosphoryl lipid A compounds (MPL® immunostimulant; Corixa Corporation; Seattle, Wash.). Methods of making and using MPL® immunostimulant, and structurally like compounds, for vaccine adjuvant and other applications have been described (see, for example, U.S. Pat. Nos. 4,436,727; 4,877,611; 4,866,034 and 4,912,094; 4,987,237; Johnson et al., *J Med Chem* 42:4640-4649 (1999); Ulrich and Myers, in *Vaccine Design: The Subunit and Adjuvant Approach*; Powell and Newman, Eds.; Plenum: New York, 495-524, 1995). In particular, these and other references demonstrated that MPL® immunostimulant and related compounds had significant adjuvant activities for enhancing humoral and/or cell-mediated immunity to the antigens, when used in vaccine formulations with protein and carbohydrate antigens.

Synthetic mono-and disaccharide molecules which share structural similarities with MPL® immunostimulant, referred to as aminoalkyl glucosaminide phosphates (AGPs), have been described, see for example, U.S. Pat. No. 6,113,918, U.S. Pat. No. 6,303,347, and WO 98/50399, published Oct. 12, 1998. These compounds retain significant adjuvant characteristics when formulated with antigens in vaccine compositions and have similar or improved toxicity profiles when compared with monophosphoryl lipid A. These compounds have been described for use in combination with antigens in vaccine formulations (U.S. Pat. No. 6,113,918) and in the absence of antigen, as monotherapies, WO 01/90129, published 29 Nov. 2001.

Cyclic aminoalkyl glucosaminide phosphates or "cyclic AGPs" have been described in PCT Patent Application No. PCT/US01/24284. These cyclic AGPs are effective immunoeffector molecules which enhance humoral and cell-mediated immune responses to vaccine antigens. As used herein, the term "cyclic AGP" means an azacycloalkyl or (azacycloalkyl) alkyl glucosaminide phosphate, wherein a 2-deoxy-2-amino-b-D-glucopyranose (glucosamine) is glycosidically linked to an azacycloalkyl or (azacycloalkyl)alkyl (aglycon) group.

The present invention provides monotherapies formulated and administered in the absence of exogenous antigens for the prophylactic and/or therapeutic treatment of plant and animal diseases and conditions, such as infectious diseases, autoimmunity and allergies. The monotherapies of the present invention comprise one or more cyclic AGPs. These and other aspects of the invention will become evident upon reference to the following detailed description and the attached drawings.

SUMMARY OF THE INVENTION

In one aspect, the present invention provides methods for treating, ameliorating or substantially preventing a disease or condition in an animal by administering an effective amount of a compound having the formula (I):

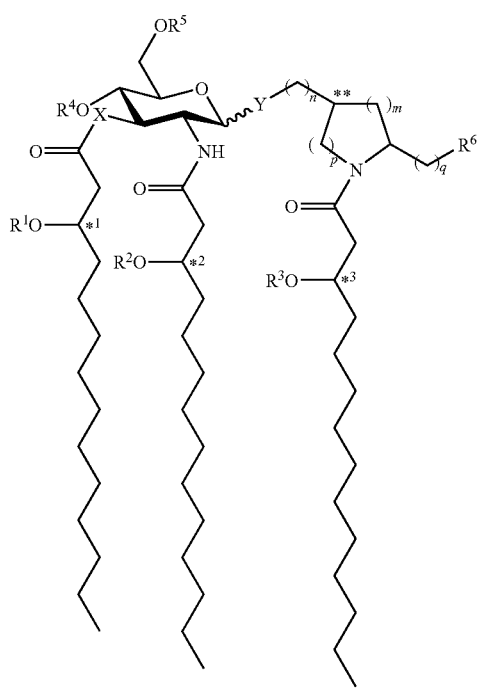

(I)

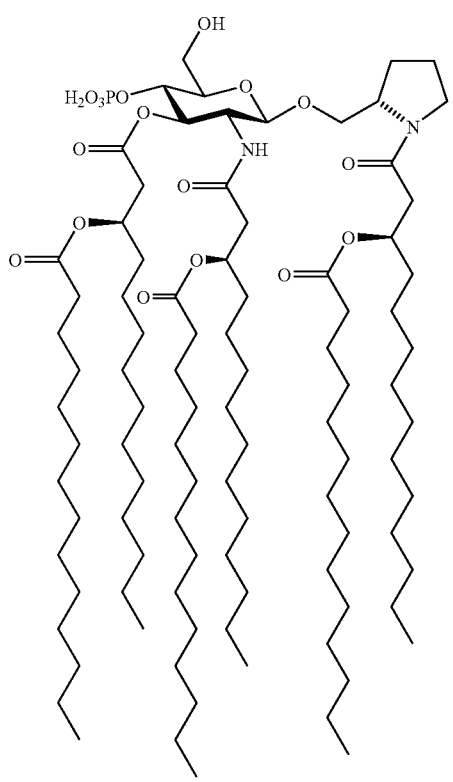

(II)

and pharmaceutically acceptable salts thereof, wherein X is —O— or —NH— and Y is —O— or —S—; $R^1$, $R^2$, and $R^3$ are each independently a ($C_2$-$C_{20}$)acyl group, including saturated, unsaturated and branched acyl groups; $R^4$ is —H or —$PO_3R^7R^8$, wherein $R^7$ and $R^8$ are each independently H or ($C_1$-$C_4$)aliphatic groups; $R^5$ is —H, —$CH_3$ or —$PO_3R^9R^{10}$, wherein $R^9$ and $R^{10}$ are each independently selected from —H and ($C_1$-$C_4$)aliphatic groups; $R^6$ is independently selected from H, OH, ($C_1$-$C_4$)oxyaliphatic groups, —$PO_3R^{11}R^{12}$, —$OPO_3R^{11}R^{12}$, —$SO_3R^{11}$, —$OSO_3R^{11}$, —$NR^{11}R^{12}$, —$SR^{11}$, —CN, —$NO_2$, —CHO, —$CO_2R^{11}$, and —$CONR^{11}R^{12}$, wherein $R^{11}$ and $R^{12}$ are each independently selected from H and ($C_1$-$C_4$)aliphatic groups; with the provisos that one of $R^4$ and $R^5$ is a phosphorus-containing group and that when $R^4$ is —$PO_3R^7R^8$, $R^5$ is other than —$PO_3R^9R^{10}$, wherein "*$^{1-3}$" and "**" represent chiral centers; wherein the subscripts n, m, p and q are each independently an integer from 0 to 6, with the proviso that the sum of p and m is from 0 to 6.

In some embodiments, the compounds of the present invention contain an —O— at X and Y, $R^4$ is $PO_3R^7R^8$, $R^5$ and $R^6$ are H, and the subscripts n, m, p, and q are integers from 0 to 3. In a more preferred embodiment, $R^7$ and $R^8$ are —H. In one embodiment, subscript n is 1, subscript m is 2, and subscripts p and q are 0. In other embodiments, $R_1$, $R_2$, and $R_3$ are ($C_6$-$C_{14}$) acyl, ($C_6$-$C_{12}$), or ($C_6$-$C_8$)acyl groups, in a particular embodiment are provided ($C_6$-$C_{12}$)acyl groups. A further embodiment provides, *$^{1-3}$ are in the R configuration, Y is in the equatorial position, and ** is in the S configuration.

Illustrative embodiments include N-[(R)-3-tetradecanoyloxytetradecanoyl]-(S)-2-pyrrolidinylmethyl 2-deoxy-4-O-phosphono-2-[(R)-3-tetradecanoyloxytetradecanoylamino]-3-O-[(R)-3-tetradecanoyloxytetradecanoyl]-β-D-glucopyranoside and pharmaceutically acceptable salts thereof; Formula II, N-[(R)-3-dodecanoyloxytetradecanoyl]-(S)-2-pyrrolidinylmethyl 2-deoxy-4-O-phosphono-2-[(R)-3-dodecanoyloxytetradecanoylamino]-3-O-[(R)-3-dodecanoyloxytetradecanoyl]-β-D-glucopyranoside and pharmaceutically acceptable salts thereof; Formula III,

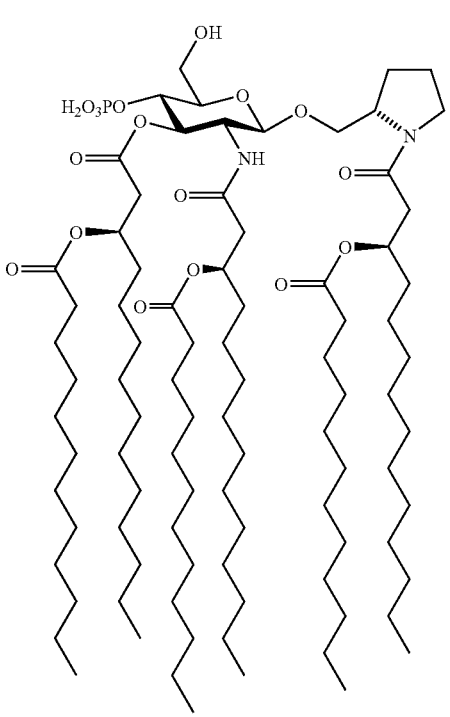

(III)

and N-[(R)-3-decanoyloxytetradecanoyl]-(S)-2-pyrrolidinylmethyl 2-deoxy-4-O-phosphono-2-[(R)-3-decanoyloxytetradecanoylamino]-3-O-[(R)-3-decanoyloxytetradecanoyl]-β-D-glucopyranoside and pharmaceutically acceptable salts thereof; Formula IV.

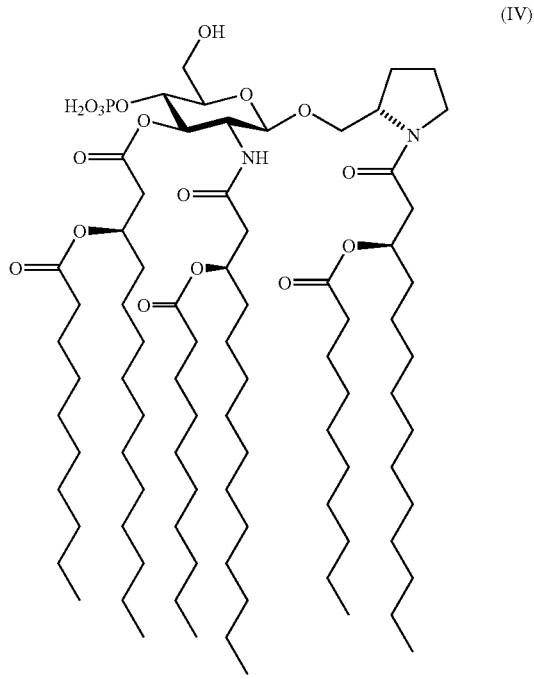

(IV)

In certain illustrative aspects of the invention, the above methods are employed in treating, ameliorating or substantially preventing infectious diseases, autoimmune diseases and allergies.

The present invention, in other aspects, provides pharmaceutical compositions comprising one or more of the compounds described above in a suitable excipient, formulated and/or administered in the absence of exogenous antigen.

DESCRIPTION OF ILLUSTRATIVE EMBODIMENTS OF THE INVENTION

Illustrative Prophylactic and Therapeutic Applications

The present invention broadly concerns prophylactic and therapeutic methods of treating certain diseases and other medical conditions by administration of an effective amount of one or more compounds described herein or a pharmaceutical composition comprising one or more such compounds. While certain of the cyclic AGP compounds have been described for use as adjuvants in combination with exogenously administered antigens in vaccine formulations, and for use in certain other applications, the present invention provides novel therapeutic methods that employ the compounds preferably in monotherapeutic applications, i.e., in the absence of exogenously administered antigen.

In one aspect the present invention provides methods for treating, ameliorating and/or substantially preventing infectious diseases in eukaryotic subjects, particularly in animals, preferably in humans. Given the importance of TLR-mediated signalling in the innate immune response to microbial challenge, the ability to stimulate such pathways selectively and with minimal toxicity represents a powerful approach for prophylactic and/or therapeutic treatment modalities against a wide range of infectious agents.

The methods described herein are applicable against essentially any type of infectious agent, including bacteria, viruses, parasites, and fungi. Illustratively, the invention is useful for the prophylactic and/or therapeutic treatment of bacterial infections by species from *Pseudomonas, Escherichia, Klebsiella, Enterobacter, Proteus, Serratia, Candida, Staphylococci, Streptococci, Chlamydia, Mycoplasma, Bacillus*, and numerous others. Illustrative viral conditions that may be treated in accordance with the invention include those caused, for example, by Influenza viruses, Adenoviruses, parainfluenza viruses, Rhinoviruses, respiratory syncytial viruses (RSVs), Herpes viruses, Cytomegaloviruses, Hepatitis viruses, e.g., Hepatitis B and C viruses, and others. Illustrative fungi include, for example, *Aspergillis, Candida albicans, Cryptococcus neoformans, Coccidioides immitus*, and others.

In one illustrative embodiment, the invention provides methods for the treatment of subjects, particularly immunocompromised subjects, that have developed or are at risk for developing infections, such as nosocomial bacterial and viral infections. About 2 million of the 40 million individuals hospitalized every year develop nosocomial infection during their stay and about 1% of these, or about 400,000 patients, develop nosocomial pneumonia, more than 7000 of which die. This makes nosocomial pneumonia the leading cause of death in hospital-acquired infections. Thus, this embodiment fills a significant need for effective prophylactic approaches in the treatment of nosocomial infections.

In a related embodiment, the present invention provides prophylactic treatments for immunocompromised patients, such as HIV-positive patients, who have developed or are at risk for developing pneumonia from either an opportunistic infection or from the reactivation of a suppressed or latent infection. In 1992, about 20,000 cases of *Pneumocystis carinii* infections in AIDS patients were reported in the U.S. alone. Additionally, 60-70% of all AIDS patients get *P. carinii* at some time during their illness. Thus, the present invention in this embodiment provides effective prophylactic methods for this at-risk population.

In another related embodiment, the methods of the present invention are used for treating other patient populations that may be immunocompromised and/or at risk for developing infectious diseases, including, for example, patients with cystic fibrosis, chronic obstructive pulmonary disease and other immunocompromized and/or institutionalized patients.

In another aspect of the invention, the compounds described herein are employed in methods for treating, ameliorating or substantially preventing allergic disorders and conditions, such as sinusitis, chronic rhinosinusitus, asthma, atopic dermatitis and psoriasis. This approach is based at least in part on the ability of the compounds to activate the production of cytokines from target cells that can compete with stereotypic allergic-type cytokine responses characterized by IL-4 production or hyperresponsiveness to IL-4 activity. Administration of certain of the compounds disclosed herein results in IFN-gamma and IL-12 expression from antigen processing and presenting cells, as well as other cells, resulting in down regulation of cytokines associated with allergic responses such as IL-4, 5, 6, 10 and 13.

In another aspect of the invention, compounds are employed in methods for treating autoimmune diseases and conditions. The compounds for use in this embodiment will typically be selected from those capable of antagonizing, inhibiting or otherwise negatively modulating one or more Toll-like receptors, particularly Tlr2 and/or Tlr4, such that an autoimmune response associated with a given condition is ameliorated or substantially prevented. Illustratively, the methods provided by this embodiment can be used in the treatment of conditions such as inflammatory bowel disease, rheumatoid arthritis, chronic arthritis, multiple sclerosis and psoriasis.

While not wishing to be bound by theory, it is believed that the efficacy of the prophylactic and therapeutic applications described above are based, at least in part on the involvement of the compounds in the modulation of Toll-like receptor activity. In particular, Toll-like receptors Tlr2, Tlr4, and others, are believed to be specifically activated, competitively inhibited or otherwise affected by the non-toxic LPS derivatives and mimetics disclosed herein. Accordingly, the methods of the invention provide a powerful and selective approach for modulating the innate immune response pathways in animals without giving rise to the toxicities often associated with the native bacterial components that normally stimulate those pathways.

Illustrative Cyclic AGP Compounds

Illustrative compounds employed in the above prophylactic and therapeutic applications comprise compounds of Formula I:

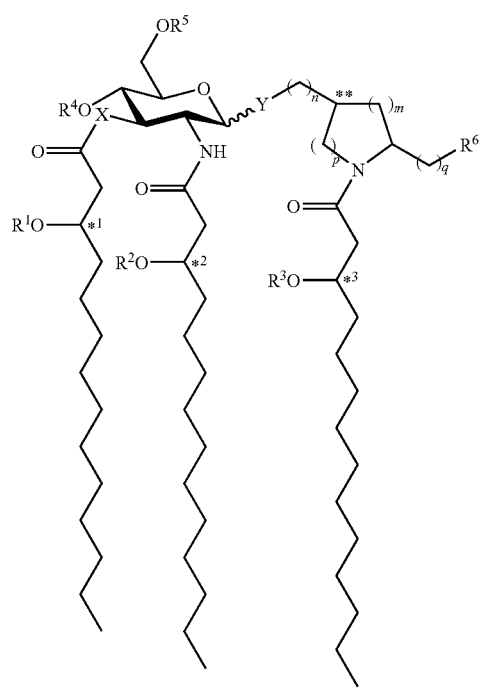

(I)

and pharmaceutically acceptable salts thereof, wherein X is —O— or —NH— and Y is —O— or —S—; $R^1$, $R^2$, and $R^3$ are each independently a ($C_2$-$C_{20}$)acyl group, including saturated, unsaturated and branched acyl groups; $R^4$ is —H or —$PO_3R^7R^8$, wherein $R^7$ and $R^8$ are each independently H or ($C_1$-$C_4$)aliphatic groups; $R^5$ is —H, —$CH_3$ or —$PO_3R^9R^{10}$, wherein $R^9$ and $R^{10}$ are each independently selected from —H and ($C_1$-$C_4$)aliphatic groups; $R^6$ is independently selected from H, OH, ($C_1$-$C_4$)oxyaliphatic groups, —$PO_3R^{11}R^{12}$, —$OPO_3R^{11}R^{12}$, —$SO_3R^{11}$, —$OSO_3R^{11}$, —$NR^{11}R^{12}$, —$SR^{11}$, —CN, —$NO_2$, —CHO, —$CO_2R^{11}$, and —$CONR^{11}R^{12}$, wherein $R^{11}$ and $R^{12}$ are each independently selected from H and ($C_1$-$C_4$)aliphatic groups; with the provisos that one of $R^4$ and $R^5$ is a phosphorus-containing group and that when $R^4$ is —$PO_3R^7R^8$, $R^5$ is other than —$PO_3R^9R^{10}$, wherein "*$^{1-3}$" and "**" represent chiral centers; wherein the subscripts n, m, p and q are each independently an integer from 0 to 6, with the proviso that the sum of p and m is from 0 to 6.

Although the hexopyranoside in Formula I is shown in the gluco configuration, other glycosides are within the scope of the invention. For example, glycopyranosides, including other hexopyranosides (e.g., allo, altro, manno, gulo, ido, galacto, talo), are within the scope of the invention.

In the general formula above, the configuration of the 3'-stereogenic centers to which the normal fatty acyl residues are attached, denoted "*$^1$", "*$^2$" and "*$^3$", is R or S, but preferably R. The absolute stereochemistry of the carbon atoms of the cyclic aglycon unit to which $R^6$ and the glucosamine unit are attached, directly or indirectly (denoted "**") can be R or S. In the general formula above, Y can be in the equatorial or axial position, but is preferably equatorial. All stereoisomers, enantiomers, diastereomers and mixtures thereof are considered to be within the scope of the present invention.

In illustrative embodiments of the present invention X and Y are —O—, $R^4$ is phosphono, $R^5$ and $R^6$ are H, and the subscripts n, m, p, and q are integers of from 0 to 3, and more preferably 0 to 2. In an exemplary embodiment the integer n is 1, the integer m is 2, and integers p and q are 0. In this embodiment, the compounds of this invention are 2-pyrrolidinylmethyl β-D-glucosaminide 4-phosphates having the general formula (V):

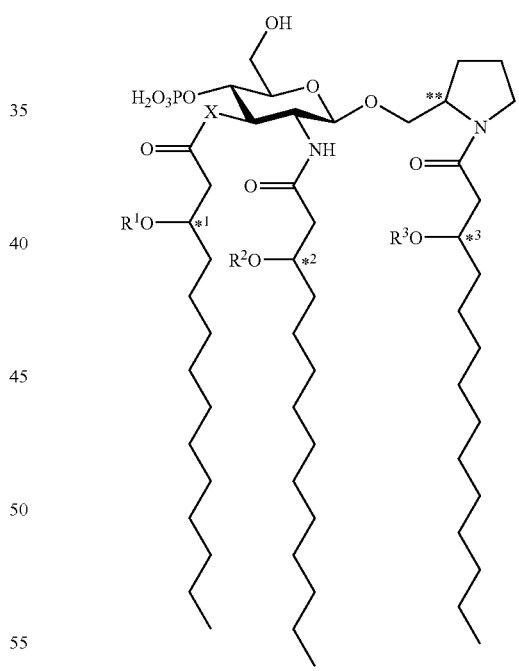

(V)

In another illustrative embodiment of the present invention, $R_1$, $R_2$, and $R_3$ of formula (III) are tetradecanoyl residues and the configuration of the 3'-stereogenic centers ("*$^{1-3}$") to which they are attached is R, Y is in the equatorial position, and the absolute stereochemistry of the pyrrolidine stereogenic center ("**") is S.

Other exemplary embodiments include N-[(R)-3-tetradecanoyloxytetradecanoyl]-(S)-2-pyrrolidinylmethyl 2-deoxy-4-O-phosphono-2-[(R)-3-tetradecanoyloxytetradecanoylamino]-3-O-[(R)-3-tetradecanoyloxytetradecanoyl]-β-D-glucopyranoside, and its pharmaceutically acceptable salts, formula (II):

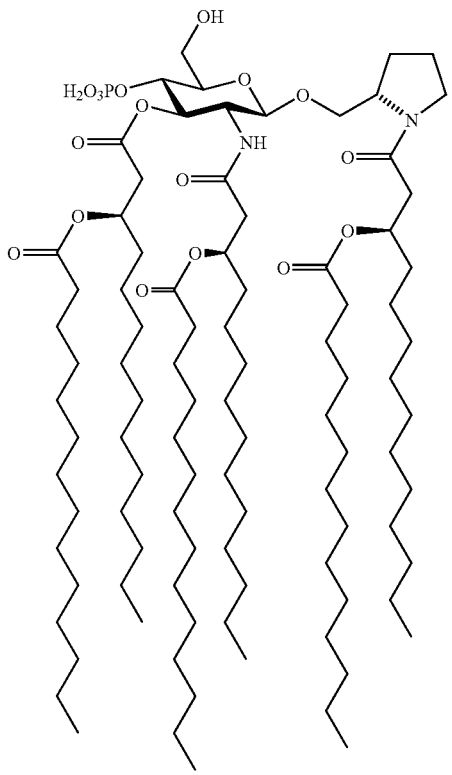

(II)

N-[(R)-3-dodecanoyloxytetradecanoyl]-(S)-2-pyrrolidinylmethyl 2-deoxy-4-O-phosphono-2-[(R)-3-dodecanoyloxytetradecanoylamino]-3-[(R)-3-dodecanoyloxytetradecanoyl]-β-D-glucopyranoside and pharmaceutically acceptable salts thereof; Formula III,

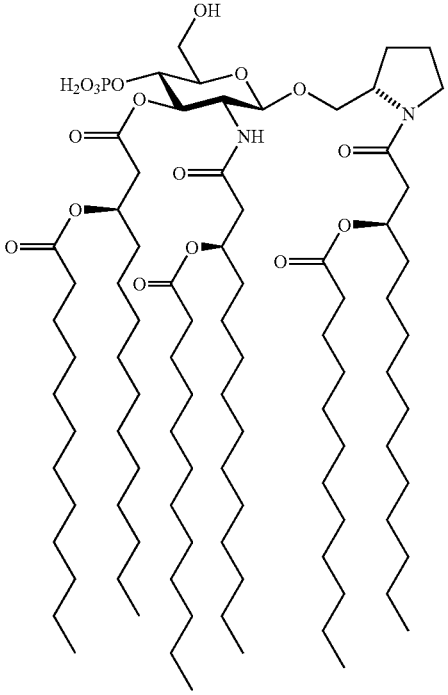

(III)

and N-[(R)-3-decanoyloxytetradecanoyl]-(S)-2-pyrrolidinylmethyl 2-deoxy-4-O-phosphono-2-[(R)-3-decanoyloxytetradecanoylamino]-3-O-[(R)-3-decanoyloxytetradecanoyl]-β-D-glucopyranoside and pharmaceutically acceptable salts thereof; Formula IV.

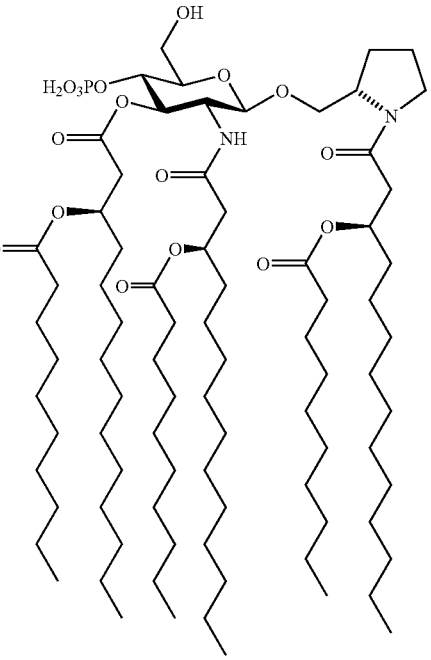

(IV)

The compounds of the present invention can be prepared using methods outlined in Johnson et al., *Bioorg. Med. Chem. Lett.* 9:2273, 1999 and PCT/WO98/50399 and references therein. In general, the synthetic methods described in the above noted reference are broadly applicable to the preparation of compounds having different acyl groups and subdivisions. For example, certain compounds useful in the present invention are described in U.S. Provisional Application No. 60/223,056 and International application PCT/US01/24284. In general, the synthetic methods described in the above-noted references described herein and other synthetic methods otherwise familiar in the art are broadly applicable to the preparation these compounds. For example, in making compounds having different acyl groups and substitutions, one of skill in the art will appreciate that the convergent methods described therein can be modified to use alternate acylating agents, or can be initiated with commercially available materials having appropriate acyl groups attached.

The term "acyl" refers to those groups derived from an aliphatic organic acid by removal of the hydroxy portion of the acid. Accordingly, acyl is meant to include, for example, acetyl, propionyl, butyryl, decanoyl, and pivaloyl.

A "$(C_2$-$C_{20})$acyl" is an acyl group having from 2 to 20 carbons. Similarly, a $(C_6$-$C_{14})$, $(C_6$-$C_{12})$, $(C_9$-$C_{12})$, and $(C_6$-$C_8)$acyl are acyl groups having from 6 to 14 carbons, from 6 to 12 carbons, from 9 to 12 carbons, and from 6 to 8 carbons, respectively. Also included within the term "acyl" are such groups having typical substituents such as hydroxy, keto, etc.

The term "aliphatic" by itself or as part of another substituent, means, unless otherwise stated, a straight or branched chain or cyclic, hydrocarbon moiety, including a moiety that contains both cyclical and chain elements, which may be fully saturated or mono-or polyunsaturated, having the number of carbon atoms designated (i.e. $C_1$-$C_4$ means one to four carbons). Examples of saturated hydrocarbon moieties include groups such as methyl, ethyl, n-propyl, isopropyl, n-butyl, t-butyl, isobutyl, sec-butyl, cyclopropyl, cyclopropylmethyl, methylene, ethylene, and n-butylene. An unsaturated alkyl group is one having one or more double and/or triple bonds. Examples of unsaturated alkyl groups include vinyl, 2-propenyl, crotyl, 1-propynyl and 2-(butadienyl).

The term "oxyaliphatic" refers to those groups having an aliphatic group attached to the remainder of the molecule through an oxygen atom.

Each of the above terms (e.g., "aliphatic," "acyl") are meant to include both substituted and unsubstituted forms of the indicated moiety. Preferred substituents for each type of group are provided below.

Substituents for the aliphatic groups can be a variety of groups selected from: —OR', =O, =S, =NR', =N—OR', —NR'R", —SR', -halogen, —SiR'R"R''', —OC(O)R', —C(O)R', —CO$_2$R', —CONR'R", —OC(O)NR'R", —NR"C(O)R', —NR'—C(O)NR"R''', —NR"C(O)$_2$R', —NH—C(NH$_2$)=NH, —NR'C(NH$_2$)=NH, —NH—C(NH$_2$)=NR', —S(O)R', —S(O)$_2$R', —S(O)$_2$NR'R", —CN and —NO$_2$ in a number ranging from zero to (2m'+1), where m' is the total number of carbon atoms in such radical. R', R" and R''' each independently refer to hydrogen and unsubstituted (C$_1$-C$_8$)aliphatic groups. When R' and R" are attached to the same nitrogen atom, they can be combined with the nitrogen atom to form a 5-, 6-, or 7-membered ring. For example, —NR'R" is meant to include 1-pyrrolidinyl and 4-morpholinyl. From the above discussion of substituents, one of skill in the art will understand that the term "aliphatic" is meant to include groups such as haloalkyl (e.g., —CF$_3$ and —CH$_2$CF$_3$) and the like.

The terms "halo" or "halogen," by themselves or as part of another substituent, mean, unless otherwise stated, a fluorine, chlorine, bromine, or iodine atom. In compounds having halogen substituents, the halogens may be the same or different.

The term "pharmaceutically acceptable salts" is meant to include salts of the active compounds which are prepared with relatively nontoxic acids or bases, depending on the particular substituents found on the compounds described herein. When compounds of the present invention contain relatively acidic functionalities, base addition salts can be obtained by addition of the desired base, either neat or in a suitable inert solvent. Examples of pharmaceutically acceptable base addition salts include sodium, potassium, calcium, ammonium, organic amino, or magnesium salt, or a similar salt. When compounds of the present invention contain relatively basic functionalities, acid addition salts can be obtained by addition of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, oxalic, maleic, malonic, benzoic, succinic, suberic, fumaric, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, for example, Berge, S. M., et al., "Pharmaceutical Salts", *Journal of Pharmaceutical Science*, 1977, 66, 1-19). Certain specific compounds of the present invention contain both basic and acidic functionalities that allow the compounds to be converted into either base or acid addition salts.

The neutral forms of the compounds may be regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present invention.

In addition to salt forms, the present invention provides compounds which are in a prodrug form. Prodrugs of the compounds described herein are those compounds that readily undergo chemical changes under physiological conditions to provide the compounds of the present invention. Additionally, prodrugs can be converted to the compounds of the present invention by chemical or biochemical methods in an ex vivo environment. For example, prodrugs can be slowly converted to the compounds of the present invention when placed in a transdermal patch reservoir with a suitable enzyme or chemical reagent.

Certain compounds of the present invention can exist in unsolvated forms as well as solvated forms, including hydrated forms. In general, the solvated forms are equivalent to unsolvated forms and are intended to be encompassed within the scope of the present invention. Certain compounds of the present invention may exist in multiple crystalline or amorphous forms. In general, all physical forms are equivalent for the uses contemplated by the present invention and are intended to be within the scope of the present invention.

Certain compounds of the present invention possess asymmetric carbon atoms (optical centers) or double bonds; the racemates, diastereomers, geometric isomers and individual isomers are all intended to be encompassed within the scope of the present invention.

The compounds of the present invention may also contain unnatural proportions of atomic isotopes at one or more of the atoms that constitute such compounds. For example, the compounds may be radiolabeled with radioactive isotopes, such as for example tritium ($^3$H), iodine-125 ($^{125}$I) or carbon-14 ($^{14}$C). All isotopic variations of the compounds of the present invention, whether radioactive or not, are intended to be encompassed within the scope of the present invention.

Illustrative Pharmaceutical Compositions and Their Delivery

In another embodiment, the present invention concerns pharmaceutical compositions comprising one or more of the compounds formulated and administered in the absence of exogenous antigen, i.e., are used in monotherapeutic applications, in combination with pharmaceutically-acceptable carriers or excipients. Such pharmaceutical compositions are useful for administration to a cell, tissue, animal or plant, either alone, or in combination with one or more other modalities of therapy. For many such embodiments, the pharmaceutical compositions of the invention will comprise one or more of the compounds described herein.

The phrase "pharmaceutically acceptable" refers to molecular entities and compositions that do not produce an allergic or similar untoward reaction when administered to a human. As used herein, "carrier" or "excipient" includes any and all solvents, dispersion media, vehicles, coatings, diluents, antibacterial and antifungal agents, isotonic and absorption delaying agents, buffers, carrier solutions, suspensions, colloids, and the like. The use of such media and agents for pharmaceutical active substances is well known in the art. Except insofar as any conventional media or agent is incompatible with the active ingredient, its use in the therapeutic compositions is contemplated.

Illustrative carriers for use in formulating the pharmaceutical compositions include, for example, oil-in-water or water-in-oil emulsions, aqueous compositions with or without inclusion of organic co-solvents suitable for intravenous (IV) use, liposomes or surfactant-containing vesicles, microspheres, microbeads and microsomes, powders, tablets, capsules, suppositories, aqueous suspensions, aerosols, and other carriers apparent to one of ordinary skill in the art.

In certain embodiments, the pharmaceutical compositions will comprise one or more buffers (e.g., neutral buffered saline or phosphate buffered saline), carbohydrates (e.g., glucose, mannose, sucrose or dextrans), mannitol, proteins, polypeptides or amino acids such as glycine, antioxidants, bacteriostats, chelating agents such as EDTA or glutathione, adjuvants (e.g., aluminum hydroxide), solutes that render the formulation isotonic, hypotonic or weakly hypertonic with the blood of a recipient, suspending agents, thickening agents and/or preservatives.

For certain applications, aqueous formulations will be preferred, particularly those comprising an effective amount of one or more surfactants. For example, the composition can be in the form of a micellar dispersion comprising at least one suitable surfactant, e.g. a phospholipid surfactant. Illustrative examples of phospholipids include diacyl phosphatidyl glycerols, such as dimyristoyl phosphatidyl glycerol (DPMG), dipalmitoyl phosphatidyl glycerol (DPPG), and distearoyl phosphatidyl glycerol (DSPG), diacyl phosphatidyl cholines, such as dimyristoyl phosphatidylcholine (DPMC), dipalmitoyl phosphatidylcholine (DPPC), and distearoyl phosphatidylcholine (DSPC); diacyl phosphatidic acids, such as dimyristoyl phosphatidic acid (DPMA), dipalmitoyl phosphatidic acid (DPPA), and distearoyl phosphatidic acid (DSPA); and diacyl phosphatidyl ethanolamines such as dimyristoyl phosphatidyl ethanolamine (DPME), dipalmitoyl phosphatidyl ethanolamine (DPPE) and distearoyl phosphatidyl ethanolamine (DSPE). Typically, a surfactant: mono-/disaccharide molar ratio in an aqueous formulation will be from about 10:1 to about 1:10, more typically from about 5:1 to about 1:5, however any effective amount of surfactant may be used in an aqueous formulation to best suit the specific objectives of interest.

As used herein, "an effective amount" is that amount which shows a response over and above the vehicle or negative controls. As discussed above, the precise dosage of the compound of the subject invention to be administered to a patient will depend the route of administration, the pharmaceutical composition, and the patient.

The compounds and pharmaceutical compositions of the invention can be formulated for essentially any route of administration, e.g., injection, inhalation by oral or intranasal routes, rectal, vaginal or intratracheal instillation, ingestion, or transdermal or transmucosal routes, and the like. In this way, the therapeutic effects attainable by the methods and compositions of the invention can be, for example, systemic, local, tissue-specific, etc., depending of the specific needs of a given application of the invention.

Illustrative formulations can be prepared and administered parenterally, i.e., intraperitoneally, subcutaneously, intramuscularly or intravenously. One illustrative example of a carrier for intravenous use includes a mixture of 10% USP ethanol, 40% USP propylene glycol or polyethylene glycol 600 and the balance USP Water for Injection (WFI). Other illustrative carriers include 10% USP ethanol and USP WFI; 0.01-0.1% triethanolamine in USP WFI; or 0.01-0.2% dipalmitoyl diphosphatidylcholine in USP WFI; and 1-10% squalene or parenteral vegetable oil-in-water emulsion. Pharmaceutically acceptable parenteral solvents will generally be selected such that they provide a solution or dispersion which may be filtered through a 0.22 micron filter without removing the active ingredient.

Illustrative examples of carriers for subcutaneous or intramuscular use include phosphate buffered saline (PBS) solution, 5% dextrose in WFI and 0.01-0.1% triethanolamine in 5% dextrose or 0.9% sodium chloride in USP WFI, or a 1 to 2 or 1 to 4 mixture of 10% USP ethanol, 40% propylene glycol and the balance an acceptable isotonic solution such as 5% dextrose or 0.9% sodium chloride; or 0.01-0.2% dipalmitoyl diphosphatidylcholine in USP WFI and 1 to 10% squalene or parenteral vegetable oil-in-water emulsions.

Examples of carriers for administration via mucosal surfaces depend upon the particular route, e.g., oral, sublingual, intranasal, etc. When administered orally, illustrative examples include pharmaceutical grades of mannitol, starch, lactose, magnesium stearate, sodium saccharide, cellulose, magnesium carbonate and the like, with mannitol being preferred. When administered intranasally, illustrative examples include polyethylene glycol, phospholipids, glycols and glycolipids, sucrose, and/or methylcellulose, powder suspensions with or without bulking agents such as lactose and preservatives such as benzalkonium chloride, EDTA. In a particularly illustrative embodiment, the phospholipid 1,2 dipalmitoyl-sn-glycero-3-phosphocholine (DPPC) is used as an isotonic aqueous carrier at about 0.01-0.2% for intranasal administration of the compound of the subject invention at a concentration of about 0.1 to 3.0 mg/ml.

When administered by inhalation, illustrative carriers include polyethylene glycol or glycols, DPPC, methylcellulose, powdered dispersing agents, and preservatives, with polyethylene glycols and DPPC being preferred. In many instances, it will be preferred that the compounds be in a nebulized form when administration by inhalation. Illustratively, delivery may be by use of a single-use delivery device, a mist nebulizer, a breath-activated powder inhaler, an aerosol metered-dose inhaler (MDI) or any other of the numerous nebulizer delivery devices available in the art. Additionally, mist tents or direct administration through endotracheal tubes may also be used. Delivery via an intratracheal or nasopharyngeal mode will be efficacious for certain indications.

One skilled in this art will recognize that the above description is illustrative rather than exhaustive. Indeed, many additional formulations techniques and pharmaceutically-acceptable excipients and carrier solutions are well-known to those skilled in the art, as is the development of suitable dosing and treatment regimens for using the particular compositions described herein in a variety of treatment regimens.

The compounds can be evaluated in a variety of assay formats, including those described herein, to identify and select those having the characteristics best suited for a given application of the invention. For example, animal models can be used for identifying and evaluating cytokine release profiles into systemic circulation following administration of a cyclic AGP compound. In addition, various in vitro and in vivo models exist for examining changes in one or more aspects of an immune response to different antigenic components in order to identify compounds best suited for eliciting a specific immune response of interest. For example, a compound can be contacted with target cells, such as macrophages, dendritic cells or Langerhans cells in vitro, and elaborated cytokines can be measured. In addition, gene expression arrays can be used to identify specific pathways activated or inhibited by a particular cyclic AGP of interest.

It will be understood that, if desired, the compounds disclosed herein may be administered in combination with other therapeutic modalities, such as antimicrobial, antiviral and antifungal compounds or therapies, various DNA-based therapeutics, RNA-based therapeutics, polypeptide-based therapeutics, and/or with other immunoeffectors. In fact, essentially any other component may also be included, given that the additional component(s) do not cause a significant adverse effect upon contact with the target cells or host tissues. The compositions may thus be delivered along with various other agents as required or desired for the specific embodiment(s) of the invention being implemented.

Illustratively, the pharmaceutical compositions of the invention can include, or be used in conjunction with, DNA encoding one or more therapeutic proteins, antisense RNAs, ribozymes or the like. The DNA may be present within any of a variety of delivery systems known to those of ordinary skill in the art, including nucleic acid expression systems, bacteria and viral expression systems. Numerous gene delivery techniques are well known in the art, such as those described by Rolland, *Crit. Rev. Therap. Drug Carrier Systems* 15:143-198, 1998, and references cited therein. Appropriate nucleic acid expression systems contain the necessary DNA sequences for expression in the patient (such as a suitable promoter and terminating signal). In a preferred embodiment, the DNA may be introduced using a viral expression system (e.g., vaccinia or other pox virus, retrovirus, or adenovirus), which may involve the use of a non-pathogenic (defective), replication competent virus. Suitable systems are disclosed, for example, in Fisher-Hoch et al., *Proc. Natl. Acad. Sci. USA* 86:317-321, 1989; Flexner et al., *Ann. N.Y. Acad. Sci.* 569: 86-103, 1989; Flexner et al., *Vaccine* 8:17-21, 1990; U.S. Pat. Nos. 4,603,112, 4,769,330, and 5,017,487; WO 89/01973; U.S. Pat. No. 4,777,127; GB 2,200,651; EP 0,345,242; WO 91/02805; Berkner, *Biotechniques* 6:616-627, 1988; Rosenfeld et al., *Science* 252:431-434, 1991; Kolls et al., *Proc. Natl. Acad. Sci. USA* 91:215-219, 1994; Kass-Eisler et al., *Proc. Natl. Acad. Sci. USA* 90:11498-11502, 1993; Guzman et al., *Circulation* 88:2838-2848, 1993; and Guzman et al., *Cir. Res.* 73:1202-1207, 1993. Techniques for incorporating DNA into such expression systems are well known to those of ordinary skill in the art.

The DNA may also be "naked," as described, for example, in Ulmer et al., *Science* 259:1745-1749, 1993 and reviewed by Cohen, *Science* 259:1691-1692, 1993. The uptake of naked DNA may be increased by coating the DNA onto biodegradable beads, which are efficiently transported into the cells. It will be apparent that a pharmaceutical composition of the invention may comprise both a polynucleotide and a protein component.

Any of a variety of additional immunostimulants may be included in the compositions of this invention. For example, cytokines, such as GM-CSF, interferons or interleukins to further modulate an immune response of interest. For example, in certain embodiments, additional components may be included in the compositions to further enhance the induction of high levels of Th1-type cytokines (e.g. IFN-$\gamma$, TNF$\alpha$, IL-2 and IL-12). Alternatively, or in addition, high levels of Th2-type cytokines (e.g., IL-4, IL-5, IL-6 and IL-10) may be desired for certain therapeutic applications. The levels of these cytokines may be readily assessed using standard assays. For a review of the families of cytokines, see Mosmann and Coffman, *Ann. Rev. Immunol.* 7:145-173, 1989.

Illustrative compositions for use in induction of Th1-type cytokines include, for example, a combination of CpG-containing oligonucleotides (in which the CpG dinucleotide is unmethylated) as described, for example, in WO 96/02555, WO 99/33488 and U.S. Pat. Nos. 6,008,200 and 5,856,462. Immunostimulatory DNA sequences are also described, for example, by Sato et al., *Science* 273:352, 1996. Other suitable immunostimulants comprise saponins, such as QS21 (Aquila Biopharmaceuticals Inc., Framingham, Mass.), GPI-100 (Marciani et al., *Vaccine* 18:3141, 2000, U.S. Pat. No. 6,080, 725) and related saponin deriviatives and mimetics thereof.

Other illustrative immunostimulants that can be used in conjunction with the present invention include Montanide ISA 720 (Seppic, France), SAF (Chiron, Calif., United States), ISCOMS (CSL), MF-59 (Chiron), the SBAS series of adjuvants (e.g., SBAS-2 or SBAS-4, available from Smith-Kline Beecham, Rixensart, Belgium), and Enhanzyn™ immunostimulant (Corixa, Hamilton, Mont.). Polyoxyethylene ether immunostimulants, are described in WO 99/52549A1.

The invention is further illustrated by the following non-limiting examples.

EXAMPLES

Examples 1

Preparation of N-[(R)-3-Tetradecanoyloxytetradecanoyl]-(S)-2-pyrrolidinylmethyl 2-Deoxy-4-O-phosphono-2-[(R)-3-tetradecanoyloxytetradecanoylamino]-3-O-[(R)-3-tetradecanoyloxytetradecanoyl]-$\beta$-D-glucopyranoside Triethylammonium Salt; Triethylammonium Salt of the Compound of Formula (II)

(1a) To a solution of 2-deoxy-4-O-diphenylphosphono-3-O-[(R)-3-tetradecanoyloxytetradecanoyl]-6-O-(2,2,2-trichloro-1,1-dimethylethoxycarbonyl)-2-(2,2,2-trichloroethoxycarbonylamino)-$\beta$-D-glucopyranosyl bromide (1.05 g, 0.81 mmol) in dry 1,2-dichloroethane (10 mL) were added 4 Å molecular sieves (0.5 g), anhydrous $CaSO_4$ (2.2 g, 16 mmol), and N-[(R)-3-tetradecanoyloxytetradecanoyl]-(S)-2-pyrrolidinemethanol (0.40 g, 0.75 mmol). The resulting mixture was stirred for 1 h at room temperature, treated with $Hg(CN)_2$ (1.02 g, 4.05 mmol), and heated to reflux for 16 h in the dark. The cooled reaction mixture was diluted with $CH_2Cl_2$ and filtered. The filtrate was washed with 1 N aq KI, dried ($Na_2SO_4$), and concentrated. Flash chromatography on silica gel (gradient elution, 15→20% EtOAc/hexanes) afforded 0.605 g (43%) of N-[(R)-3-tetradecanoyloxytetradecanoyl]-(S)-2-pyrrolidinylmethyl 2-deoxy-4-O-diphenylphosphono-3-O-[(R)-3-tetradecanoyloxytetradecanoyl]-6-O-(2,2,2-trichloro-1,1-dimethylethoxycarbonyl)-2-(2,2,2-trichloroethoxycarbonylamino)-$\beta$-D-glucopyranoside as an amorphous solid.

(1b) A solution of the compound prepared in (1a) above (0.50 g, 0.29 mmol) in AcOH (10 mL) at 60° C. was treated with zinc dust (0.98 g, 15 mmol) in three equal portions over a 1-h period. The cooled reaction mixture was sonicated, filtered through a pad of Celite, and concentrated. The resulting residue was partitioned between $CH_2Cl_2$ and saturated aq $NaHCO_3$, and the layers were separated. The organic layer was dried ($Na_2SO_4$) and concentrated. A solution of the crude amino alcohol obtained and (R)-3-tetradecanoyloxytetradecanoic acid (0.155 g, 0.34 mmol) in $CH_2Cl_2$ (3.5 mL) was stirred with powdered 4 Å molecular sieves (0.25 g) for 0.5 h and then treated with 2-ethoxy-1-ethoxycarbonyl-1,2-dihydroquinoline (0.11 g, 0.44 mmol). The resulting mixture was stirred at room temperature for 8 h, filtered through Celite, and concentrated. Flash chromatography on silica gel with 50% EtOAc/hexanes gave 0.355 g (68%) of N-[(R)-3-tetradecanoyloxytetradecanoyl]-(S)-2-pyrrolidinylmethyl 2-deoxy-4-O-diphenylphosphono-2-[(R)-3-tetradecanoyloxytetradecanoylamino]-3-O-[(R)-3-tetradecanoyloxytetradecanoyl]-β-D-glucopyranoside as a colorless syrup.

(1c) A solution of the compound prepared in (1b) above (0.300 g, 0.166 mmol) in a mixture of AcOH (1 mL) and tetrahydrofuran (9 mL) was hydrogenated in the presence of $PtO_2$ (0.15 g) at room temperature and 70 psig for 18 h. The reaction mixture was diluted with 2:1 $CHCl_3$—MeOH (50 mL) and sonicated briefly. The catalyst was collected and washed with 2:1 $CHCl_3$—MeOH and the combined filtrate and washings were concentrated. Flash chromatography on silica gel with $CHCl_3$—MeOH—$H_2O$—$Et_3N$ (90:10:0.5:0.5) gave partially purified product which was dissolved in ice-cold 2:1 $CHCl_3$—MeOH (30 mL) and washed with ice-cold 0.1 N aq HCl (12 mL). The organic phase was filtered and lyophilized from 2% aq $Et_3N$ (5 mL, pyrogen-free) to give 0.228 g (79%) of N-[(R)-3-tetradecanoyloxytetradecanoyl]-(S)-2-pyrrolidinylmethyl 2-deoxy-4-O-phosphono-2-[(R)-3-tetradecanoyloxytetradecanoylamino]-3-O-[(R)-3-tetradecanoyloxytetradecanoyl]-β-D-glucopyranoside triethylammonium salt as a colorless powder: mp 67-70° C.; IR (film) 3306, 2955, 2923, 2853, 1736, 1732, 1644, 1548, 1466, 1378, 1245, 1177, 1110, 1053, 844 cm$^{-1}$; $^1$H NMR ($CDCl_3$-$CD_3OD$) δ 0.88 (m, 18 H), 1.0-1.2.05 (mH), 2.20-2.70 (m, 12 H), 3.06 (q, 6 H, J=7.2 Hz), 3.3-325 (mH), 4.52 (d, 1 H, J=8 Hz), 5.05-5.28 (m, 4 H), 7.44 (d, 1 H, J=9 Hz); $^{13}$C NMR ($CDCl_3$) δ 173.3, 173.0, 170.3, 169.6, 168.6, 101.8, 100.4, 75.8, 72.5, 72.4, 70.9, 70.8, 70.3, 70.2, 69.9, 69.3, 67.9, 66.6, 56.5, 56.3, 54.5, 47.4, 45.8, 44.6, 41.4, 41.0, 39.7, 39.2, 39.0, 34.5, 34.3, 34.1, 32.0, 29.7, 29.4, 28.1, 27.3, 25.7, 25.3, 25.2, 25.1, 24.0, 22.7, 21.6, 14.1, 8.6.

Anal. Calcd. for $C_{101}H_{194}N_3O_{17}P\cdot H_2O$: C, 68.47; H, 11.15; N, 2.37; P, 1.75. Found: C, 68.79; H, 11.00; N, 2.24; P, 1.97.

Example 2

Preparation of N-[(R)-3-Dodecanoyloxytetradecanoyl]-(S)-2-pyrrolidinylmethyl 2-Deoxy-4-O-phosphono-2-[(R)-3-dodecanoyloxy-tetradecanoylamino]-3-O-[(R)-3-dodecanoyloxytetradecanoyl]-β-D-glucopyranoside Triethylammonium Salt); Triethylammonium Salt of Formula (III)

(2a) To a solution of 2-deoxy-4-O-diphenylphosphono-3-O-[(R)-3-dodecanoyloxytetradecanoyl]-6-O-(2,2,2-trichloro-1,1-dimethylethoxycarbonyl)-2-(2,2,2-trichloroethoxycarbonylamino)-α-D-glucopyranosyl bromide (1.60 g, 1.27 mmol) in dry 1,2-dichloroethane (3.2 mL) were added 4 Å molecular sieves (0.6 g), anhydrous $CaSO_4$ (1.0 g, 7.3 mmol), and N-[(R)-3-dodecanoyloxytetradecanoyl]-(S)-2-pyrrolidinemethanol (0.58 g, 1.14 mmol). The resulting mixture was stirred for 1 h at room temperature, treated with $Hg(CN)_2$ (0.58 g, 2.3 mmol), and heated to reflux for 6 h in the dark. The cooled reaction mixture was diluted with $CH_2Cl_2$ and filtered through a bed of celite. The filtrate was washed with 1 N aq KI, dried ($Na_2SO_4$), and concentrated. Flash chromatography on silica gel (gradient elution, 25→35% EtOAc/hexanes) afforded 1.72 g (82%) of N-[(R)-3-dodecanoyloxytetradecanoyl]-(S)-2-pyrrolidinylmethyl 2-deoxy-4-O-diphenylphosphono-3-O-[(R)-3-dodecanoyloxytetradecanoyl]-6-O-(2,2,2-trichloro-1,1-dimethylethoxycarbonyl)-2-(2,2,2-trichloroethoxycarbonylamino)-β-D-glucopyranoside as a colorless oil.

(2b) A solution of the compound prepared in (2a) above (1.58 g, 0.806 mmol) in AcOH (40 mL) at 60° C. was treated with zinc dust (2.6 g, 40 mmol) in three equal portions over a 1-h period. The cooled reaction mixture was sonicated, filtered through a pad of Celite, and concentrated. The resulting residue was partitioned between EtOAc and saturated aq $NaHCO_3$ and the layers separated. The organic layer was washed with brine, dried ($Na_2SO_4$), and concentrated to give 1.3 g of a white solid. A solution of the crude amino alcohol obtained and (R)-3-dodecanoyloxytetradecanoic acid (0.45 g, 1.05 mmol) in $CH_2Cl_2$ (20 mL) was treated with 2-ethoxy-1-ethoxycarbonyl-1,2-dihydroquinoline (0.30 g, 1.21 mmol). The resulting mixture was stirred at room temperature for 18 h and concentrated. Flash chromatography on silica gel with 40→50% EtOAc/hexanes gave 0.89 g (56%) of N-[(R)-3-dodecanoyloxytetradecanoyl]-(S)-2-pyrrolidinylmethyl 2-deoxy-4-O-diphenylphosphono-2-[(R)-3-dodecanoyloxytetra-decanoylamino]-3-O-[(R)-3-dodecanoyloxytetradecanoyl]-β-D-glucopyranoside as a white foam.

(2c) A solution of the compound prepared in (2b) above (0.75 g, 0.44 mmol) in a mixture of AcOH (4.5 mL) and tetrahydrofuran (45 mL) was hydrogenated in the presence of $PtO_2$ (0.45 g) at room temperature and 70 psig for 18 h. The reaction mixture was diluted with 2:1 $CHCl_3$—MeOH (35 mL) and sonicated briefly. The catalyst was collected and washed with 2:1 $CHCl_3$—MeOH and the combined filtrate and washings were concentrated. Flash chromatography on silica gel with $CHCl_3$—MeOH—$H_2O$—$Et_3N$ (gradient elution; 96:4:0.3:0.3→90:10:0.5:0.5) gave partially purified product (0.51 g) which was dissolved in ice-cold 2:1 $CHCl_3$—MeOH (50 mL) and washed with ice-cold 0.1 N aq HCl (20 mL). The organic phase was filtered and concentrated. The white wax obtained was lyophilized from 2% aq $Et_3N$ (70 mL, pyrogen-free) to give 0.54 g (78%) of N-[(R)-3-dodecanoyloxytetradecanoyl]-(S)-2-pyrrolidinylmethyl 2-deoxy-4-O-phosphono-2-[(R)-3-dodecanoyloxytetradecanoylamino]-3-O-[(R)-3-dodecanoyloxy-tetradecanoyl]-β-D-glucopyranoside triethylammonium salt as a white powder: mp 146-151° C.; IR (film) 3292, 3100, 2958, 2922, 2852, 1739, 1731, 1659, 1651, 1644, 1562, 1555, 1468, 1455, 1433, 1377, 1339, 1310, 1253, 1238, 1183, 1160, 1107, 1080, 1047, 960, 856, 722 cm$^{-1}$; $^1$H NMR ($CDCl_3$—$CD_3OD$) δ 0.88 (m, 18 H), 1.0-2.10 (mH), 2.20-2.75 (m, 12 H), 3.04 (q, 6 H, J=7.2 Hz), 3.3-4.3 (mH), 4.45 (d, 1 H, J=8.5 Hz), 5.0-5.28 (m, 4 H); $^{13}$C NMR ($CDCl_3$) δ 173.9, 173.4, 173.2, 170.6, 170.1, 169.2, 101.4, 75.5, 74.0, 70.8, 70.7, 70.2, 68.5, 60.5, 56.6, 53.6, 47.4, 45.6, 40.9, 39.6, 38.8, 34.5, 34.3, 34.2, 34.1, 31.9, 29.7, 29.6, 29.5, 29.4, 29.4, 29.3, 29.2, 27.3, 25.2, 25.0, 23.6, 22.7, 21.6, 14.0, 8.3.

MALDI-MS calculated for [M+Na]$^+$ 1590.1900, found 1590.1866; Anal. Calculated for $C_{95}H_{182}N_3O_{17}P\cdot 3H_2O$: C, 66.20; H, 10.99; N, 2.44. Found: C, 66.36; H, 10.69; N, 2.15.

Example 3

Preparation of N-[(R)-3-Decanoyloxytetradecanoyl]-(S)-2-pyrrolidinylmethyl 2-Deoxy-4-O-phosphono-2-[(R)-3-Decanoyloxytetradecanoylamino]-3-O-[(R)-3-Decanoyloxytetradecanoyl]-β-D-glucopyranoside Triethylammonium Salt; Triethylammonium Salt of Formula (IV)

(3a) To a solution of 2-deoxy-4-O-diphenylphosphono-3-O-[(R)-3-decanoyloxytetradecanoyl]-6-O-(2,2,2-trichloro-1,1-dimethylethoxycarbonyl)-2-(2,2,2-trichloroethoxycarbonylamino)-α-D-glucopyranosyl bromide (1.70 g, 1.38 mmol) in dry 1,2-dichloroethane (3.5 mL) were added 4 Å molecular sieves (0.6 g), anhydrous $CaSO_4$ (1.2 g, 8.8 mmol), and N-[(R)-3-decanoyloxytetradecanoyl]-(S)-2-pyrrolidinemethanol (0.60 g, 1.24 mmol). The resulting mixture was stirred for 1 h at room temperature, treated with $Hg(CN)_2$ (0.63 g, 2.5 mmol), and heated to reflux for 6 h in the dark. The cooled reaction mixture was diluted with $CH_2Cl_2$ and filtered through a bed of celite. The filtrate was washed with 1 N aq KI, dried ($Na_2SO_4$), and concentrated. Flash chromatography on silica gel (gradient elution, 25→40% EtOAc/hexanes) afforded 1.82 g (80%) of N-[(R)-3-decanoyloxytetradecanoyl]-(S)-2-pyrrolidinylmethyl 2-deoxy-4-O-diphenylphosphono-3-O-[(R)-3-decanoyloxytetradecanoyl]-6-O-(2,2,2-trichloro-1,1-dimethylethoxycarbonyl)-2-(2,2,2-trichloroethoxycarbonylamino)-β-D-glucopyranoside as a colorless oil.

(3b) A solution of the compound prepared in (3a) above (1.67 g, 1.02 mmol) in AcOH (50 mL) at 60° C. was treated with zinc dust (3.33 g, 51 mmol) in three equal portions over a 1-h period. The cooled reaction mixture was sonicated, filtered through a pad of Celite, and concentrated. The resulting residue was partitioned between EtOAc and saturated aq $NaHCO_3$ and the layers separated. The organic layer was washed with brine, dried ($Na_2SO_4$), and concentrated to give 1.25 g of a white solid. A solution of the crude amino alcohol obtained and (R)-3-decanoyloxytetradecanoic acid (0.53 g, 1.33 mmol) in $CH_2Cl_2$ (20 mL) was treated with 2-ethoxy-1-ethoxycarbonyl-1,2-dihydroquinoline (0.38 g, 1.53 mmol). The resulting mixture was stirred at room temperature for 18 h and concentrated. Flash chromatography on silica gel with 40→50% EtOAc/hexanes gave 1.23 g (74%) of N-[(R)-3-decanoyloxytetradecanoyl]-(S)-2-pyrrolidinylmethyl 2-deoxy-4-O-diphenylphosphono-2-[(R)-3-decanoyloxytetradec-anoylamino]-3-O-[(R)-3-decanoyloxytetradecanoyl]-β-D-glucopyranoside as a white foam.

(3c) A solution of the compound prepared in (3b) above (1.07 g, 0.654 mmol) in a mixture of AcOH (6.5 mL) and tetrahydrofuran (65 mL) was hydrogenated in the presence of $PtO_2$ (0.66 g) at room temperature and 70 psig for 18 h. The reaction mixture was diluted with 2:1 $CHCl_3$—MeOH (50 mL) and sonicated briefly. The catalyst was collected and washed with 2:1 $CHCl_3$—MeOH and the combined filtrate and washings were concentrated. The resulting waxy solid obtained was lyophilized from 2% aq triethylamine to give ~1 g of the crude triethylammonium salt as a white powder. Flash chromatography on silica gel with $CHCl_3$—MeOH—$H_2O$—$Et_3N$ (gradient elution; 96:4:0.3:0.3→88:12:1:0.6) gave partially purified product (0.84 g) which was dissolved in ice-cold 2:1 $CHCl_3$—MeOH (168 mL) and washed with ice-cold 0.1 N aq HCl (67 mL). The organic phase was filtered and concentrated. The white wax obtained (~0.7 g) was lyophilized from 2% aq $Et_3N$ (70 mL, pyrogen-free) to give 0.79 g (79%) of N-[(R)-3-decanoyloxytetradecanoyl]-(S)-2-pyrrolidinylmethyl 2-deoxy-4-O-phosphono-2-[(R)-3-decanoyloxytetradecanoylamino]-3-O-[(R)-3-decanoyloxytetradecanoyl]-β-D-glucopyranoside triethylammonium salt as a white powder: mp 121-122° C.; IR (film) 3287, 3093, 2961, 2913, 2850, 1745, 1738, 1732, 1716, 1666, 1660, 1651, 1644, 1635, 1565, 1556, 1538, 1470, 1455, 1434, 1416, 1378, 1337, 1311, 1248, 1184, 1104, 1081, 1021, 964, 721 $cm^{-1}$; $^1$H NMR (CDCl3-$CD_3OD$) δ 0.88 (m, 18 H), 1.0-2.05 (mH), 2.20-2.75 (m, 12 H), 3.04 (q, 6 H, J=7.2 Hz), 3.3-4.3 (mH), 4.45 (d, 1 H, J=8.5 Hz), 5.0-5.28 (m, 4 H); $^{13}$C NMR ($CDCl_3$) δ 173.7, 173.4, 173.2, 170.5, 170.1, 169.1, 101.4, 75.6, 74.0, 70.8, 70.2, 68.7, 60.4, 56.5, 53.8, 47.4, 45.6, 41.0, 39.6, 38.9, 34.5, 34.3, 34.2, 34.1, 31.9, 29.7, 29.6, 29.5, 29.4, 29.4, 29.3, 29.2, 27.3, 25.3, 25.0, 23.7, 22.7, 21.6, 14.1, 8.4.

MALDI-MS calcd for [M+Na]$^+$ 1506.0961, found 1506.1008; Anal. Calcd. for $C_{89}H_{170}N_3O_{17}P$: C, 67.43; H, 10.81; N, 2.65. Found: C, 67.26; H, 10.85; N, 2.47.

Example 4

Murine *Listeria monocytogenes* Challenge Model

This example provides experiments evaluating the induction of non-specific resistance in the murine *Listeria monocytogenes* challenge model performed using the compounds prepared in examples 1, 2 and 3. Mice (5 per group) were treated intravenously with the 1 μg of a cyclic AGP or MPL solublized in 0.2% triethanolamine (TEOA). Two days later the mice were challenged intravenously with a ~10$^5$ *L. monocytogenes* 10403 serotype (stock culture provided by Jory Baldridge, Washington State University, Pullman, Wash.). Two days after the challenge the mice were sacrificed and the number of colony forming units (CFUs) in the spleens of individual mice were determined by plating 10-fold serial dilutions of splenic homogenates on tryptic soy agar plates. The degree of protection afforded by a given AGP or MPL was calculated by subtracting the average number of bacteria per spleen (log 10 value) in the group of mice treated with a given compound, from the average number of bacteria per spleen (log 10 value) in a control group that was "sham" treated with vehicle (0.2% TEOA) prior to challenge with *L. monocytogenes*.

Of the compounds tested, that of Example 3 was the most active, inducing protection that was comparable to MPL (~0.9 log 10 units). The compound of example 2 induced slightly less protection and that of example 1 was the least protective, (0.7 and 0.2 log units, respectively).

Example 5

Protection Against Lethal Influenza Challenge by Prophylactic Administration of Cyclic AGPs This example provides experiments evaluating protection against a lethal challenge with influenza in cyclic AGP-treated mice. BALB/c mice (10 mice per group) were treated intranasally with 20 μg of the compounds of examples 1, 2 and 3, or with MPL, 48 hours prior to an lethal intranasal challenge of Influenza A/HK/68 (5 LD50). Protection was judged by survival, observations of clinical symptoms (ruffled fur, hunched posture and labored breathing), and prevention of weight loss for 21 days following the challenge.

As was seen in the *Listeria* model, the compounds of examples 2 and 3 provided enhanced protection when compared with the vehicle control. Mice treated with the compound of example 3 had a 60% survival rate; those treated with the compound of example 2 had a 40% survival rate, and those with MPL, a 30% survival rate. No mice treated with the compound of example 1 survived. These data indicate that the compound of example 3 provided superior protection, followed by those of examples 2 and 1.

All publications and patent applications cited in this specification are herein incorporated by reference in their entirety. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A method for inducing an innate immune response in a subject, the method comprising administering to the subject an effective amount of one or more compounds having the formula:

(I)

and a pharmaceutically acceptable salts thereof, wherein X is a member selected from the group consisting of —O— and —NH—;
Y is a member selected from the group consisting of —O— and —S—;
$R^1$, $R^2$ and $R^3$ are each members independently selected from the group consisting of $(C_6-C_{12})$ acyl;
$R^4$ is a member selected from the group consisting of —H and —$PO_3R^7R^8$, wherein $R^7$ and $R^8$ are each members independently selected from the group consisting of —H and $(C_1-C_4)$aliphatic groups;
$R^5$ is a member selected from the group consisting of —H, —$CH_3$ and —$PO_3R^9R^{10}$, wherein $R^9$ and $R^{10}$ are each members independently selected from the group consisting of —H and $(C_1-C_4)$aliphatic groups;
$R^6$ is selected from H, OH, $(C_1-C_4)$oxyaliphatic groups, —$PO_3R^{11}R^{12}$, —$OPO_3R^{11}R^{12}$, —$SO_3R^{11}$, —$OSO_3R^{11}$, —$NR^{11}R^{12}$, —$SR^{11}$, —CN, —$NO_2$, —CHO, —$CO_2R^{11}$, and —$CONR^{11}R^{12}$, wherein $R^{11}$ and $R^{12}$ are each independently selected from H and $(C_1-C_4)$aliphatic groups, with the provisos that one of $R^4$ and $R^5$ is a phosphorus-containing group and that when $R^4$ is —$PO_3R^7R^8$, $R^5$ is other than —$PO_3R^9R^{10}$;
wherein "*1", "*2", "*3" and "**" represent chiral centers;
wherein n, m, p and q are each independently an integer from 0 to 6, with the proviso that the sum of p and m is from 0 to 6; and
wherein the compound is administered in the absence of an exogenous antigen.

2. The method of claim 1, wherein X and Y are —O—, $R^4$ is $PO_3R^7R^8$, $R^5$ and $R^6$ are H, and n, m, p, and q are integers from 0 to 3.

3. The method of claim 2, wherein $R^7$ and $R^8$ are —H.

4. The method of claim 2, wherein n, m, p, and q are from 0 to 2.

5. The method of claim 3, wherein n is 1, m is 2, and p and q are 0.

6. The method of claim 1, wherein $R_1$, $R_2$; and $R_3$ are each $C_9-C_{12}$ acyl.

7. The method of claim 5, wherein $R_1$, $R_2$, and $R_3$ are each decanoyl residues.

8. The method of claim 5, wherein $R_1$, $R_2$, and $R_3$ are each dodecanoyl residues.

9. The method of claim 5, wherein *1, *2, and *3 are in the R configuration.

10. The method of claim 5, wherein Y is in the equatorial position.

11. The method of claim 5, wherein ** is in the S configuration.

12. The method of claim 5, wherein *1, *2, and *3 are in the R configuration, wherein Y is in the equatorial position, and wherein ** is in the S configuration.

13. The method of claim 1, wherein the subject has an infectious disease caused by a bacterium or a virus.

14. The method of claim 13, wherein said bacterium is a gram negative bacterium or a gram positive bacterium.

15. The method of claim 13, wherein the infectious disease is caused by a bacterium selected from the group consisting of *Pseudomonas*, *Escherichia*, *Klebsiella*, *Enterobacter*, *Proteus*, *Serratia*, *Candida*, *Bacillus*, and *Staphylococcus*.

16. The method of claim 15, wherein the infectious disease is pneumonia.

17. The method of claim 16, wherein said pneumonia is nosocomial pneumonia.

* * * * *